United States Patent [19] [11] Patent Number: 4,705,880
Alper et al. [45] Date of Patent: Nov. 10, 1987

[54] CARBONYLATION OF MERCAPTANS

[75] Inventors: Howard Alper, Ottawa, Canada; David J. H. Smith, Camberley, England

[73] Assignee: The British Petroleum Company p.l.c., London, England

[21] Appl. No.: 870,187

[22] Filed: Jun. 3, 1986

[30] Foreign Application Priority Data

Jun. 4, 1985 [GB] United Kingdom ............... 8514008

[51] Int. Cl.[4] ............... C07C 153/017; C07C 153/023
[52] U.S. Cl. ..................................... 558/257; 558/250
[58] Field of Search ............................. 558/250, 257

[56] References Cited

U.S. PATENT DOCUMENTS 3,933,884   1/1976   Knifton ........................... 558/250

Primary Examiner—Richard A. Schwartz
Assistant Examiner—Robert C. Whittenbaugh
Attorney, Agent, or Firm—Brooks Haidt Haffner & Delahunty

[57] ABSTRACT

Thioesters of the formula RCOSR are produced from a mercaptan of the formula RSH wherein R is a benzylic, aromatic or aliphatic moiety by reacting the mercaptan with carbon monoxide in the presence of a polyunsaturated olefinic hydrocarbon and as catalyst a metal component selected from iron, cobalt, nickel, molybdenum, ruthenium, rhodium and iridium, the metal component being in free or combined form.

10 Claims, No Drawings

CARBONYLATION OF MERCAPTANS

The present invention relates to a process for the carbonylation of mercaptans. More specifically the invention relates to the production of thioesters of the general formula RCOSR by the catalysed carbonylation of mercaptans of the formula RSH wherein R is a benzylic, aromatic or aliphatic moiety.

Many investigations have been carried out on metal catalysed reactions of substrates bearing nitrogen and oxygen atoms. Examples include the cobalt carbonyl catalysed reductive carbonylation of Schiff bases with organoboranes (Alper, H; Amaratunga, S., *J. Org. Chem.*, 1982, 47, 3593), the conversion of amines to formamides or ureas induced by various metal complexes (Sheldon, R. A. "Chemicals from synthesis gas", D. Reidel Publishing Co., Dordrecht, Holland, pp 167–184) and the ruthenium catalysed carbonylation of methyl ether to methyl acetate (Braca et al, *J. Am. Chem. Soc.*, 1978, 100, 6238). Few examples are known of catalytic processes in which one of the reactants contains sulphur as the heteroatom, since the presence of such a heteroatom frequently poisons the catalysts.

Because of the long-term potential of the availability of carbon monoxide as a reactant, a vast amount of research has been recently directed towards its utilisation in chemical synthesis. For example, commercial processes have been developed for the production of acetic acid by the reaction of methanol and carbon monoxide and to the production of acetic anhydride by the reaction of methyl acetate and carbon monoxide. These developments provide impetus for the search for a catalytic carbonylation process which both utilises a reactant containing sulphur and which also utilises carbon monoxide.

As early as 1963, W. Reppe in Ann., 582, 1 (1953) and W. Reppe and H. Kroper in Ann., 582, 38 (1953) reported the reactions of carbon monoxide with thiols in the presence of either acetylene or an olefin as a third component. The products obtained were the thiol esters of the carbonylated unsaturate, not those of the direct reaction of carbon monoxide with thiols.

Thereafter, Holmquist, H. E. and Carnahan, J. E. reported in *J. Org. Chem.*, 25, 2240-2 (1960) the reaction of thiols, disulphides and sulphides with carbon monoxide to give thiol esters in accordance with equations 1–3 in the presence of a cobalt carbonyl catalyst or certain metal oxide catalysts at 250°–300° C. and 100–1000 atm.

2RSH+CO→R COS R+H₂S (1)

RSSR+2CO→R COS R+COS (2)

RSR+CO→R COS R (3)

They also reported that an important competing reaction to thiol ester formation was the reduction of thiol to hydrocarbon according to the equation (4).

RSH+CO→RH+COS (4)

Generally, low yields of the thiol esters were obtained by Holmquist and Carnahan.

We have found that the reaction of mercaptans with carbon monoxide can lead to a variety of products depending upon the nature of the reaction conditions chosen. Thus, we have found that cobalt carbonyl is an excellent catalyst for the desulphurisation and carbonylation of benzylic mercaptans and thiophenols to carboxylic esters. This forms the subject matter of our copending European application publication No. 0146291 (BP Case No. 5745). On the other hand, hydrocarbons were formed when the reaction was effected in benzene instead of aqueous alcohol. This forms the subject of our copending European application publication No. 0167261 (BP Case No. 5851).

We have now surprisingly found that the reaction of a benzylic, aromatic or aliphatic mercaptan with carbon monoxide in the presence as catalyst of a variety of metals, including cobalt, can produce the corresponding thioester in high yields with substantially no hydrocarbon formation and under milder conditions than those reported previously, when the reaction is carried out in the presence of a polyunsaturated olefinic hydrocarbon, such as for example a diene.

Accordingly, the present invention provides a process for the production of thioesters of the formula R COS R from a mercaptan of the formula RSH wherein R is a benzylic, aromatic or aliphatic moiety which process comprises reacting the mercaptan with carbon monoxide in the presence of a polyunsaturated olefinic hydrocarbon and as catalyst a metal component selected from iron, cobalt, nickel, molybdenum, ruthenium, rhodium and iridium, the metal component being in free or combined form.

In the formula RSH, R is either a benzylic, an aromatic or an aliphtic moiety. The benzylic moiety is of general formula:

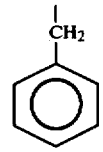

and may be substituted in the benzene nucleus portion thereof by, for example, hydrocarbyl groups such as by alkyl groups or by functional groups such as halide or alkoxy groups. Examples of benzylic mercaptans include, but are not limited to, p-methylbenzyl mercaptan, o-methylbenzyl mercaptan, p-methylbenzyl mercaptan, p-chlorobenzyl mercaptan, 2,4-dichlorobenzyl mercaptan, and the like.

The aromatic moiety may be either substituted or unsubstituted and includes aryl, arylene and multiply substituted moieties. The substituted aromatic moiety may be substituted with, for example, alkyl, alkenyl or halide groups. Examples of aromatic mercaptans include, but are not limited to, m-toluenethiol, p-bromothiophenol, 2-napthalenethiol, phenylthiol and the like.

The aliphatic moiety may be straight-chained or branch-chained saturated or unsaturated, substituted or unsubstituted. Generally, the aliphatic moiety may be from 1 to 20 carbon atoms, preferably from 2 to 12 carbons atoms. Suitable substituents on the aliphatic moiety include halide and alkoxy groups. Examples of aliphatic mercaptans include, but are not limited to, methanethiol, ethanethiol, butanethiol, butenethiol, 3-chloropropyl mercaptan and the like. A preferred aliphatic mercaptan is methanethiol.

Carbon monoxide may be obtained from a variety of carbonaceous sources using conventional conversion technology. The carbon monoxide may be pure or may contain impurities such as carbon dioxide, nitrogen and the like. Synthesis gas containing predominantly carbon monoxide may also be employed as a source of carbon monoxide.

The metal component of the catalyst system of the present invention is selected from the metals iron, cobalt, nickel, molybdenum, ruthenium, rhodium and iridium with cobalt being preferred. The metal component may be a metal or metal compound such as a metal salt and is preferably a metal carbonyl compound. The metal salt or metal carbonyl compound may be added as such or may be formed under reaction conditions either during the reaction or in a separate preparative step in the absence of the reactants. Suitable metal compounds are metal salts such as a metal nitrate, chloride or acetate.

A cobalt carbonyl compound, for example, is suitably added in an amount between 0.1 to about 20% by weight of metal based on the total weight of mercaptan employed.

The polyunsaturated olefinic hydrocarbons used as the second component of the catalyst system of the present invention are suitably $C_4$ to $C_{30}$ cyclic or acyclic hydrocarbons containing at least two carbon-carbon double bonds. The double bonds can be cummulative (double bonds which connect at least three carbon atoms) or, preferably, can be conjugated. The unsaturated hydrocarbons preferred herein are alkadienes or alkatrienes having 4 to 20 carbon atoms and which are straight-chained, branched or cyclic. Most preferably, the unsaturated hydrocarbon will be an alkadiene, including compounds such as indene, butadiene, 2-methyl-1,3-butadiene, 1,3-cyclohexadiene, 2,3-dimethyl-1,3-butadiene, 2,3-dimethoxy-1,3-butadiene and the like of which 2,3-dimethyl-1,3-butadiene and 2,3-dimethoxy-1,3-butadiene are preferred and the latter is more preferred. The process may be operated in the presence or absence of water, preferably in the presence of water.

Whilst the reaction may suitably be effected in the absence of a solvent, it may also be effected in the presence of a solvent. Suitable solvents include hydrocarbon solvents and particularly aromatic hydrocarbon solvents, e.g. benzene. The process may be operated in the presence or absence of water, preferably in the presence of water.

The temperature of the reaction is suitably elevated and preferably, the pressure is also elevated. Temperatures in the range from 10° to 300° C., preferably from 150° to 250° C. have been found suitable. Pressures in the range from 2 to 200 atmospheres, particularly from 20 to 100 atmospheres are preferred.

While not intending to be bound to theory, it is believed that the unsaturated hydrocarbon component of the catalyst system can complex to the metal component to generate a catalyst species, perhaps by the interception of an organometallic intermediate.

Thus, in a separate embodiment of the present invention, unsaturated hydrocarbon-metal carbonyl complexes can be employed as a catalyst in the carbonylation reaction as described herein. Such complexes are known in the art and can be prepared by the conventional reaction of an unsaturated hydrocarbon with a metal carbonyl compound.

One method of preparing a complex active as a catalyst in the process of the present invention is described in *J. Chem. Soc.*, 1961, 602 by Winkhaus, G. and Wilkinson, G. J., which description is incorporated by reference herein. Another method of preparing an unsaturated hydrocarbon-metal carbonyl complex is disclosed by McArdle, P.,; Manning A. R., in *J. Chem. Soc.*, (A), 1970, 2123. The complex can be prepared in situ or separately and then placed into the carbonylation reaction.

The products of the present invention are thioesters, sulphides and hydrocarbons in varying ratios depending upon the specific conditions chosen.

While the process of the present invention may be operated batchwise, it is preferably operated in a continuous manner.

The invention will now be further illustrated by reference to the following examples. However, these examples are merely illustrative of the present invention which includes equivalent modifications, variations and embodiments, and should not be construed as limiting the scope thereof.

EXAMPLES 1-16

The following general procedure was used for each example. A mixture of the mercaptan (10 mmol), diene (10-12 mmol), cobalt carbonyl (0.5 mmol), water (2 ml.) and benzene (30 ml.) was heated overnight at 185°-190° C. and 55-61 atm. After cooling to room temperature, the mixture was analysed by gas chromatography, and then worked-up by distillation or by column chromatography. The results are shown in the Table.

TABLE 1

Products Obtained from the Reaction of Mercaptans with Diene, CO, and $Co_2(CO)_8$

| Example | RSH,R = | Diene[a] | Thioester RCOSR | Di-sulphide | Addition Product | Sulphide |
|---|---|---|---|---|---|---|
| 1 | Ph | CHD | 20 | 10 | | |
| 2 | | DME | 87 | 3 | | |
| 3 | p-$CH_3C_6H_4$ | CHD | 22 | 16 | 6 | |
| 4 | | In | 37 | 15 | 20 | |
| 5 | | DM | 61 | 5 | 3 | |
| 6 | | DME | 82 | 4 | | |
| 7 | p-$CH_3OC_6H_4$ | CHD | 24 | 27 | | |
| 8 | | DM | 58 | . | 14 | |
| 9 | p-$BrC_6H_4$ | DM | 55 · | 4 | 12 | |
| 10 | p-$FC_6H_4$ | CHD | 24 | 5 | | |
| 11 | | DME | 84 | 5 | | |
| 12 | 2-$C_{10}H_7$ | CHD | 24 | 27 | | |
| 13 | | DM | 63 | | 14 | |
| 14 | | DME | 85 | 2 | | |
| 15 | p-$CH_3OC_6H_4CH_2$ | CHD | 13 | 5 | | 55 |

Products, % Yield[b]

TABLE 1-continued

Products Obtained from the Reaction of Mercaptans with Diene, CO, and $Co_2(CO)_8$

| Example | RSH, R = | Diene[a] | Thioester RCOSR | Di-sulphide | Addition Product | Sulphide |
|---|---|---|---|---|---|---|
| 16 | | DME | 59 | 12 | 3 | |

[a] CHD = 1,3-cyclohexadiene, In = indene, 45 DM = 2,3-dimethyl-1,3-butadiene, DME = 2,3-dimethoxyl-1,3-butadiene.
[b] Products were identified by comparison of boiling points and spectral data (ir, nmr[$^1$H, $^{13}$C], ms) with literature values. Yields are of pure materials.

EXAMPLE 17

The diene-cobalt carbonyl complex:

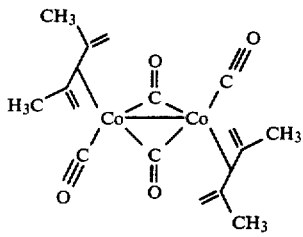

was synthesised by the method described in *J. Chem. Soc.*, 1961, 602 by Winkhaus, G. and Wilkinson, G. J.

The complex was employed as the catalyst for the carbonylation of p-methyoxybenzenethiol in benzene using the method described in Examples 1 to 8, except that no diene and $Co_2CO_3$ was added. The thioester was obtained in 48% yield, which compares favourably with the yield (58%) obtained using diene and $Co_2CO_3$ added separately.

EXAMPLE 18

The procedure of Examples 1 to 16 was repeated using methanethiol, as the mercaptan.

The corresponding thioester and acetic acid were detected in the products.

We claim:

1. A process for the production of thioesters of the formula R COS R from a mercaptan of the formula RSH wherein R is a benzylic, aromatic or aliphatic moiety which process comprises reacting the mercaptan with carbon monoxide in the presence of a catalyst system comprising a polyunsaturated olefinic hydrocarbon catalyst component and a metal catalyst component selected from the group consisting of iron, cobalt, nickel, molybdenum, ruthenium, rhodium and iridium, the metal component being in free or combined form.

2. A process according to claim 1 wherein the metal component is cobalt.

3. A process according to claim 2 wherein the metal component is in the form of the metal carbonyl.

4. A process according to claim 1 wherein the polyunsaturated olefinic hydrocarbon is a $C_4$ to $C_{30}$ cyclic or acyclic hydrocarbon containing at least two carbon-carbon double bonds.

5. A process according to claim 4 wherein the double bonds are conjugated double bonds.

6. A process according to claim 1 wherein the polyunsaturated olefinic hydrocarbon is an alkadiene or alkatriene having 4 to 20 carbon atoms and which is straight-chain, branched-chain or cyclic.

7. The process according to claim 1 wherein the polyunsaturated olefinic hydrocarbon is either 2,3-dimethyl-1,3-butadiene or 2,3-dimethoxy-1,3-butadiene.

8. A process according to claim 1 wherein the metal component of the catalyst and the polyunsaturated olefinic hydrocarbon are added in the form of a polyunsaturated olefinic hydrocarbon-metal carbonyl complex.

9. A process according to claim 1 wherein the mercaptan is methanethiol.

10. A process according to claim 1 wherein the reaction is carried out at a temperature in the range from 150° to 250° C. and a pressure in the range from 20 to 100 atmospheres.

* * * * *

UNITED STATES PATENT AND TRADEMARK OFFICE
CERTIFICATE OF CORRECTION

PATENT NO. : 4,705,880

DATED : November 10, 1987

INVENTOR(S) : HOWARD ALPER and DAVID J. H. SMITH

It is certified that error appears in the above-identified patent and that said Letters Patent is hereby corrected as shown below:

Claim 7, line 1, change "The" to -- A --.

Signed and Sealed this

Twenty-first Day of June, 1988

Attest:

DONALD J. QUIGG

*Attesting Officer*   *Commissioner of Patents and Trademarks*